United States Patent
Klee et al.

(10) Patent No.: US 9,993,395 B2
(45) Date of Patent: Jun. 12, 2018

(54) POLYMER FOR A GLASS IONOMER CEMENT

(75) Inventors: Joachim E. Klee, Radolfzell (DE); Helmut Ritter, Wuppertal (DE); Maximilliam Maier, Düsseldorf (DE); Julia Gansel, Radolfzell (DE); Andreas Facher, Gundetswill (DE); Oliver Elsner, Allensbach (DE); Sven Pohle, Konstanz (DE)

(73) Assignee: DENTSPLY SIRONA Inc., York, PA (US)

( * ) Notice: Subject to any disclaimer, the term of this patent is extended or adjusted under 35 U.S.C. 154(b) by 266 days.

(21) Appl. No.: 13/988,049

(22) PCT Filed: Dec. 20, 2011

(86) PCT No.: PCT/EP2011/006446
§ 371 (c)(1),
(2), (4) Date: Jul. 19, 2013

(87) PCT Pub. No.: WO2012/084206
PCT Pub. Date: Jun. 28, 2012

(65) Prior Publication Data
US 2013/0289216 A1    Oct. 31, 2013

(30) Foreign Application Priority Data
Dec. 22, 2010  (EP) .................... 10015981

(51) Int. Cl.
| | | |
|---|---|---|
| *C08F 8/00* | (2006.01) | |
| *A61K 6/083* | (2006.01) | |
| *C08F 8/12* | (2006.01) | |
| *C08F 8/46* | (2006.01) | |

(52) U.S. Cl.
CPC .............. *A61K 6/0835* (2013.01); *C08F 8/00* (2013.01); *C08F 8/12* (2013.01); *C08F 8/46* (2013.01)

(58) Field of Classification Search
CPC . A61K 6/0835; C08F 8/00; C08F 8/46; C08F 220/12; C08F 220/06; C08F 220/18; C08L 33/08; C08L 33/10
See application file for complete search history.

(56) References Cited

U.S. PATENT DOCUMENTS

| | | | |
|---|---|---|---|
| 3,655,605 A | 4/1972 | Smith et al. | |
| 3,814,717 A | 6/1974 | Wilson et al. | |
| 4,072,529 A * | 2/1978 | Hoornstra et al. | ......... 430/286.1 |
| 4,089,830 A | 5/1978 | Tezuka et al. | |
| 4,143,018 A | 3/1979 | Crisp et al. | |
| 4,209,434 A | 6/1980 | Wilson et al. | |
| 4,317,681 A | 3/1982 | Beede et al. | |
| 4,360,605 A | 11/1982 | Schmitt et al. | |
| 4,374,936 A | 2/1983 | Tomioka et al. | |
| 4,376,835 A | 3/1983 | Schmitt et al. | |
| 5,130,347 A * | 7/1992 | Mitra | ........................... 522/149 |

FOREIGN PATENT DOCUMENTS

| | | |
|---|---|---|
| WO | 2003011232 A1 | 2/2003 |
| WO | 2003061606 A1 | 7/2003 |
| WO | 2009023843 A1 | 2/2009 |
| WO | 2012084206 A1 | 6/2012 |

OTHER PUBLICATIONS

Chen et al & Nesterova et al(Chen et al.,Journal of Applied Polymer Science, 109(2008) 2802-2807).
N.A. Nesterova et alter, Russian Journal of Applied Chemistry 2009, vol. 82, No. 4, pp. 618-621.
K. Yamamoto et alter, Journal of Applied Polymer Science 2002, vol. 89, pp. 1277-1283.
International Search Report, Application No. 2011/006446, dated Dec. 20, 2011.
International Written opinion, Application No. 2011/006446, dated Dec. 20, 2011.

* cited by examiner

Primary Examiner — Mark S Kaucher
(74) Attorney, Agent, or Firm — Sushma Chauhan; Douglas J. Hura; Leana Levin

(57) ABSTRACT

A process for producing a water-soluble, hydrolysis-stable, polymerizable polymer, comprising a) a step of copolymerizing a mixture comprising (i) a first copolymerizable monomer comprising at least one optionally protected carboxylic acid group and a first polymerizable organic moiety, and (ii) a second copolymerizable monomer comprising one or more optionally protected primary and/or secondary amino groups and a second polymerizable organic moiety, for obtaining an amino group containing copolymer; b) a step of coupling to the amino group containing copolymer a compound having a polymerizable moiety and a functional group reactive with an amino group of repeating units derived from the second copolymerizable monomer in the amino group containing copolymer obtained in the first step wherein the optionally protected amino group is deprotected, so that polymerizable pendant groups are linked to the backbone by hydrolysis-stable linking groups, and, optionally, a step of deprotecting the protected carboxylic acid group after step (a) or step (b), for obtaining a polymerizable polymer.

13 Claims, No Drawings

POLYMER FOR A GLASS IONOMER CEMENT

FIELD OF THE INVENTION

The present invention relates to a process for the production of a water-soluble, hydrolysis-stable and polymerizable polymer for a glass ionomer cement. Moreover, the present invention relates to an polymer for a glass ionomer cement, which is obtainable by the process of the present invention and a dental composition comprising the polymer for a glass ionomer cement. Furthermore, the present invention relates to the use of the polymer for the preparation of a dental composition, in particular a dental cement.

According to the process of the present invention, it is possible to conveniently and efficiently obtain a hydrolysis-stable and polymerizable polymer for a glass ionomer cement at a high molecular weight, which is resistant to acidic media and capable of further crosslinking providing improved storage stability and long-term mechanical resistance of a dental ionomer cement.

BACKGROUND OF THE INVENTION

WO03011232 discloses resin-modified glass ionomer cements containing a polymer having a plurality of acidic repeating units and a plurality of polymerizable vinyl groups which can be formed in one method by partially reacting a material such as a polymeric acid anhydride with a monomer containing an acid- or acid anhydride-reactive group and containing one or more vinyl groups that will provide the desired polymerizable functionality. The acid- or acid anhydride-reactive group reacts with acid units or anhydride units in a the polymeric precursor to provide pendant vinyl groups in the resulting reaction product so that a hydrolyzable polymer is obtained. Another method involves copolymerizing an α,β-unsaturated carboxylic acid and a suitable α,β-unsaturated monomer containing one or more such pendant vinyl groups, whereby a crosslinked product cannot be avoided.

WO03061606 discloses ionomeric cements containing a polymerizable ionomer which is obtainable based on three carboxylic acid monomers, two of which are acrylic acid and itaconic acid, and the third monomer is an acryloyl- or methacryloyl derivative of an amino acid, whereby polymerizable pendant groups are not linked to the backbone by hydrolysis-stable linking groups.

Dental restorative materials are known for restoring the function, morphology and integrity of dental structures damaged by physical damage or caries-related decay of enamel and/or dentin. Dental restorative materials can be divided into two classes, indirect restorative materials and direct restorative materials.

Indirect restorations such as inlays, onlays, crowns or bridges are adhered to the damaged residual hard dental tissue with a specific dental composition, such as a dental resin cement. Adequate adhesion of the restoration typically requires the application of a primer as a pre-treatment step.

Direct restorative materials, such as dental composites are applied directly onto the dental surface and subsequently cured in situ. However, direct restorations often require pre-treatment with an adhesive or primer to enhance adhesive strength.

Common to all dental restorations is that they require high biocompatibility, resistance to the severe conditions present in the oral cavity, particularly over a longer period of time.

Glass ionomer cements (GIC), which are cured by an acid-base reaction between silicate glass powder and a polyalkenoic acid, provide high biocompatibility, good direct adhesion to the dental hard tissues and cariostatic properties through the release of fluoride ions and are widely used as direct dental restorative materials.

However, conventional glass ionomer cements are relatively brittle due to low flexural strength properties. The resistance of glass ionomer cements to mechanical stress may be improved by the choice of the polymer for a glass ionomer cement. For example, a polymer for a glass ionomer cement, which has polymerizable moieties as pendant groups can be crosslinked to increase the mechanical resistance of the resulting glass ionomer cement.

Moreover, for the purpose of the cement reaction as well as for providing adhesive properties of the dental composition to hard dental tissue, acidic groups in the polymer are required. However, acidic groups accelerate hydrolysis of pendant functional groups linked to the polymer backbone by hydrolysable groups such as ester groups. Thus, a polymer to be used in a dental composition desirably has a plurality of carboxylic acid groups and at the same time a high stability with regard to hydrolysis in order to avoid degradation of the composition during storage or when applied to hard dental tissue.

Japanese Patent Publication No. 2005-65902A discloses a dental adhesive composition comprising, as a polymerizable monomer containing a particular carboxylic acid, a carboxylic acid compound having a (meth)acryloyl group and a carboxyl group which are bound to an aromatic group. However, such a polymerizable monomer having an ester group quickly degrades in an acidic medium.

Chen et al. and Nesterova et al. (Chen et al., J. Appl. Polym. Sci., 109 (2008) 2802-2807; Nesterova et al., Russian Journal of Applied Chemistry, 82 (2009) 618-621) disclose copolymers of N-vinylformamide with acrylic acid and/or methacrylic acid, respectively. However, none of these documents mentions the introduction of a further polymerizable moiety into the copolymer.

WO2003/011232 discloses water-based medical and dental cements that can be post-polymerized after the cement reaction. The dental cements consist of two separate polymers, wherein one of the polymers has a pendant post-polymerizable moiety linked to the polymer through an ester bond. However, this ester bond between the polymer and the polymerizable moieties is again prone to hydrolytic cleavage in acidic media. Moreover, crosslinking of the glass ionomer may lead to the shrinkage of the dental composition in particular when the molecular weight of the crosslinking polymer is low.

SUMMARY OF THE INVENTION

It is an object of the present invention to provide a process for preparing a polymer for a dental composition, wherein the polymer has good adhesive strength to dental hard tissue, high stability against hydrolysis in an acidic medium and wherein the polymer may be crosslinked during curing for improving the mechanical resistance of the dental cement, and whereby shrinkage stress during polymerization of the dental composition during crosslinking is reduced or even avoided whereby the problem of shrinkage of the dental composition during curing is alleviated.

The present invention provides a process for producing a water-soluble, hydrolysis-stable, polymerizable polymer, comprising a) a step of copolymerizing a mixture comprising
   (i) a first copolymerizable monomer comprising at least one optionally protected carboxylic acid group and a first polymerizable organic moiety, and
   (ii) a second copolymerizable monomer comprising one or more optionally protected primary and/or secondary amino groups and a second polymerizable organic moiety,
   for obtaining an amino group containing copolymer;
b) a step of coupling to the amino group containing copolymer a compound having a polymerizable moiety and a functional group reactive with an amino group of repeating units derived from the second copolymerizable monomer in the amino group containing copolymer obtained in the first step wherein the optionally protected amino group is deprotected, and, optionally, a step of deprotecting the protected carboxylic acid group after step (a) or step (b), for obtaining a polymerizable polymer.

Specifically, in the step of coupling to the amino group containing copolymer a compound having a polymerizable moiety and a functional group reactive with an amino group of repeating units derived from the second copolymerizable monomer in the amino group containing copolymer obtained in the first step, the polymerizable pendant groups are linked to the backbone by hydrolysis-stable linking groups. The linkage preferably does not contain an ester group.

Moreover, the present invention provides a polymer obtainable by the process as defined above.

Furthermore, the present invention provides a dental composition comprising the polymer as defined above.

Finally, the present invention provides a use of a polymer as defined above for the preparation of a dental composition.

The process of the present invention provides a polymer useful in a glass ionomer cement, which is hydrolysis-stable and can be polymerized to yield a dental glass ionomer cement of improved mechanical resistance. The polymer may be provided with a high amount of acidic groups resulting in an excellent adhesion to dental hard tissue. Moreover, since the process of the present invention provides a polymer having a high molecular weight, any polymer shrinkage during the curing reaction may be easily controlled.

The present inventors have recognized that resin reinforced dental glass ionomer cements are subject to deterioration during storage or after curing in the mouth of the patient. The present inventors have further recognized that the deterioration is due to hydrolytic degradation of the resin component conventionally containing hydrolyzable moieties. The present inventors have then recognized that by using a specific process for the preparation of a polymer, an improved water-soluble, hydrolysis-stable, polymerizable polymer may be prepared at a high molecular weight which overcomes the drawbacks of conventional resin reinforced glass ionomer cements known from the prior art. In particular, the present invention is based on the recognition that the introduction of amino group containing repeating units into the backbone of the polymer opens up the possibility to provide high molecular weight copolymers which may be easily and efficiently functionalized by the introduction of polymerizable pendant groups linked to the backbone by hydrolysis stable linking groups so that the disadvantages of conventional polymerizable resin components may be avoided. Based on the unique and unexpected effect of the orientation of the amino carbonyl group present in the polymer of the present invention in relation to the polymer backbone and the pendant groups, the present invention was accomplished.

According to the present invention, a two-step process is required wherein the step of forming an amino group containing copolymer by addition polymerizing a monomer mixture is separate from a step of introducing polymerizing pendant groups in a polymer analog reaction in order to avoid crosslinking of the polymer backbone.

DESCRIPTION OF THE PREFERRED EMBODIMENTS

The process for the preparation of a water-soluble, hydrolysis-stable, polymerizable polymer according to the present invention comprises for obtaining a polymerizable polymer a step a) and a step b), and optionally a step c).

Generally, a polymer for a glass ionomer cement is an organic polymeric compound comprising ionizable pendant groups, such as carboxylic acid groups. The carboxylic acid groups of a polymer can react with a suitable glass component to form a glass ionomer cement which can be used as a dental material.

A "polymerizable polymer for a glass ionomer cement" according to the present invention is a polymer containing one or more polymerizable moieties allowing polymerization and crosslinking of the polymer after the formation of a glass ionomer cement, increasing the long-term mechanical resistance of the material.

Herein, "water-soluble" means that at least 0.1 g, preferably 0.5 g of the polymer dissolves in 100 g of water at 20° C.

"Hydrolysis-stable" means that the polymer is stable to hydrolysis in an acidic medium, such as in a dental composition. Specifically, the polymer does not contain groups such as ester groups which hydrolyze in aqueous media at pH3 at room temperature within one month.

Step a) of the process of the present invention is a step of copolymerizing a mixture comprising a first copolymerizable monomer comprising at least one optionally protected carboxylic acid group and a first polymerizable organic moiety and a second copolymerizable monomer comprising one or more optionally protected primary and/or secondary amino groups and a second polymerizable organic moiety for obtaining an amino group containing copolymer. The mixture may also contain further monomers.

The first copolymerizable monomer to be used in step a) comprises at least one, preferably one to three, more preferably one or two, most preferably one optionally protected carboxylic acid group(s).

The protecting group of an optionally protected carboxylic acid group is not particularly limited as long as it is a carboxyl-protecting group known to those of ordinary skill in the art of organic chemistry (cf. P. G. M. Wuts and T. W. Greene, Greene's Protective Groups in Organic Synthesis, 4th Edition, John Wiley and Sons Inc., 2007). Preferably, the carboxyl-protecting group is selected from a trialkylsilyl group, an alkyl group and an arylalkyl group. More preferably, the carboxyl-protecting group is selected from an alkyl group or an arylalkyl group. Most preferably, the carboxyl-protecting group is selected from a tert-butyl group and a benzyl group. In one preferred embodiment, the carboxyl-protecting group is a tert-butyl group.

A polymerizable organic moiety is an organic moiety of a molecule which can be used to covalently link this molecule in a chemical reaction (polymerization) to other molecules reactive with this moiety to form a macromolecule of repeating or alternating structural units. Preferably, this polymerizable organic moiety is a carbon-carbon double bond as in the case of an ethylenically unsaturated moiety.

In a preferred embodiment of the process of the present invention, the first copolymerizable monomer is represented by the general formula (1):

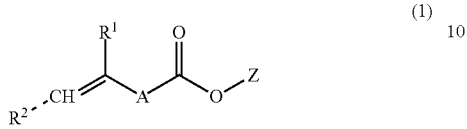

In formula (1), $R^1$ is a hydrogen atom, a —COOZ group or a straight chain or branched $C_{1-6}$ alkyl group which may be substituted by a —COOZ group. Preferably, $R^1$ is a hydrogen atom, a —COOZ group or a methyl group. More preferably, $R^1$ is a hydrogen atom or a methyl group.

In formula (1), $R^2$ is a hydrogen atom, a —COOZ group or a straight-chain or branched $C_{1-6}$ alkyl group which may be substituted by a —COOZ group. Preferably, $R^2$ is a hydrogen atom or a —COOZ group. More preferably, $R^2$ is a hydrogen atom. In formula (1), the dotted line indicates that $R^2$ may be in either the cis or trans orientation.

In formula (1), A is a single bond or a straight-chain or branched $C_{1-6}$ alkylene group which group may contain 1 to 3 heteroatoms in between two carbon atoms of the alkylene carbon chain, which heteroatoms are selected from an oxygen atom, nitrogen atom, and sulfur atom, and/or which alkylene group may contain in between two carbon atoms of the alkylene carbon chain 1 to 3 groups selected from an amide bond or a urethane bond. Preferably, A is a single bond or a straight-chain or branched $C_{1-6}$ alkylene group which group may contain a heteroatom in between two carbon atoms of the alkylene carbon chain, which heteroatom is selected from an oxygen atom or a nitrogen atom, and/or which alkylene group may contain in between two carbon atoms of the alkylene carbon chain a group selected from an amide bond or a urethane bond. More preferably, A is a single bond or a straight-chain $C_{1-6}$ alkylene group. Most preferably, A is a single bond.

In formula (1), Z which may be the same or different independently represents a hydrogen atom, a metal ion, a protecting group for a carboxylic acid group, or the Z forms with a further —COOZ group present in the molecule an intramolecular anhydride group. The metal ion may be a monovalent metal ion such as an alkali metal ion. In one embodiment, Z is a protecting group for a carboxylic acid group. In another embodiment, Z is a hydrogen atom.

When Z forms with a further —COOZ group present in the molecule an intramolecular anhydride group (—C(O)OC(O)—), the further —COOZ group may be preferably present on $R^1$ such as in case of itaconic acid anhydride.

In a preferred embodiment, Z is a hydrogen atom and the polymerization reaction is conducted in an alkaline environment. In an alternative preferred embodiment, Z is a hydrogen atom and the amino groups of the first copolymerizable monomer and of the second copolymerizable monomer carry a protecting group.

Preferably, a first copolymerizable monomer is a protected (meth)acrylic acid monomer. More preferably, a first polymerizable monomer is selected from tert-butyl acrylate and benzyl acrylate. Most preferably, a first polymerizable monomer is tert-butyl acrylate.

In a preferred embodiment of the process of the present invention, the second copolymerizable monomer is represented by the general formula (2):

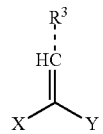

In formula (2), $R^3$ is a hydrogen atom or a straight chain or branched $C_{1-6}$ alkyl group which may be substituted by a —COOZ' group. Preferably, $R^3$ is a hydrogen atom. In formula (2), the dotted line indicates that $R^3$ may be in either the cis or trans orientation.

In formula (2), X is a protected amino group or a hydrocarbon group having 1 to 20 carbon atoms, which is substituted with an amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. Preferably, X is a hydrocarbon group having 1 to 20 carbon atoms, which is substituted with an amino group which may carry a protecting group, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, X is a hydrocarbon group having 1 to 20 carbon atoms, even more preferably 1 to 6 carbon atoms, which is substituted with an amino group which may carry a protecting group, wherein the hydrocarbon group may contain an oxygen atom and/or which hydrocarbon group may contain an amide bond and which hydrocarbon group may further be substituted with a —COOZ' group. In as specific embodiment wherein X is a protected amino group, the compound of formula (2) is allyl amine, wherein the amino group carries a protecting group.

The protecting group of a protected amino group or an optionally protected amino group is not particularly limited and may be any conventional protecting group for an amino group as, for example, described in P. G. M. Wuts and T. W. Greene, Greene's Protective Groups in Organic Synthesis, 4th Edition, John Wiley and Sons Inc., 2007. Preferably, the amino-protecting group is selected from an acyl group, an arylalkyl group, an alkoxy carbonyl group, and an aryloxycarbonyl group. More preferably, the amino-protecting group is an acyl group. Most preferably, the amino-protecting group is a formyl group.

In formula (2), Y is a hydrogen atom or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. Preferably, Y is a hydrogen atom or a hydrocarbon group having 1 to 20 carbon atoms, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, Y is a hydrogen atom or a hydrocarbon group having 1 to 20 carbon atoms, even more preferably 1 to 6 carbon atoms, wherein the hydrocarbon group may contain an oxygen atom and/or which hydrocarbon group may contain an amide bond and which hydrocarbon group may further be substituted with a —COOZ' group. In one preferred embodiment, Y is a hydrogen atom.

In formula (2), Z' which may be the same or different, independently represents a hydrogen atom, a metal ion, a protecting group for a carboxylic acid group, or the Z' forms with a further —COOZ' group present in the molecule an intramolecular anhydride group. In one embodiment, Z' is a protecting group for a carboxylic acid group. In another embodiment, Z' is a hydrogen atom. The metal ion may be a monovalent metal ion such as an alkali metal ion. In another embodiment, Z' is a hydrogen atom. When Z forms with a further —COOZ' group present in the molecule an intramolecular anhydride group (—C(O)OC(O)—).

In a preferred embodiment, Z' is a hydrogen atom and the polymerization reaction is conducted in an alkaline environment. In an alternative preferred embodiment, Z' is a hydrogen atom and the amino groups of the second copolymerizable monomer carry a protecting group.

In one embodiment, the second copolymerizable monomer comprises a second copolymerizable organic moiety selected from the group of (meth)acrylamide moieties which may be substituted and substituted (meth)acrylic acid which may be protected. In another embodiment, the second copolymerizable monomer is selected from allyl amine, aminopropyl vinyl ether, aminoethyl vinyl ether, N-vinyl formamide and 2-aminomethyl acrylic acid. In a preferred embodiment, the second copolymerizable monomer is aminopropyl vinyl ether. The amino group may be in the form of an ammonium salt such as a ammonium chloride. Preferred structures are as follows wherein the amino group may also carry a protecting group:

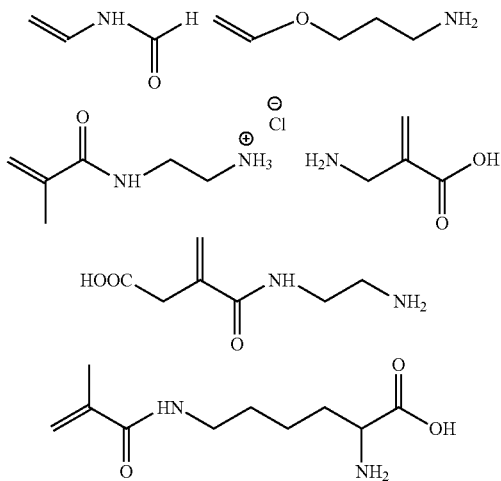

The molar ratio of first copolymerizable monomer and second copolymerizable monomer in the mixture copolymerized in step (a) (mol first copolymerizable monomer/mol second copolymerizable monomer) is in the range of from 100:5 to 5:100, preferably in the range from 50:5 to 5:20, more preferably in the range from 40:5 to 1:1.

The further copolymerizable monomers optionally to be used in step a) comprise at least one, preferably one to three, more preferably one or two, most preferably one optionally protected acidic group(s) which are not carboxylic acid groups. Specific examples of acidic groups are sulfonic acid groups (—$SO_3M$), phosphonic acid groups (—$PO_3M_2$) or phosphoric acid ester groups (—$OPO_3M._2$), or salts thereof, wherein M may independently be a hydrogen atom or a monovalent ion such as an alkali metal or an ammonium ion.

Specific examples of the optional further monomers are selected from 2-Acrylamido-2-methylpropane sulfonic acid, vinyl phosphonate, and vinyl sulfonic acid.

In a preferred embodiment, the solutions containing the first copolymerizable monomer and the second copolymerizable monomer are separately saturated with nitrogen before combining them for copolymerization to minimize possible side-products of a competitive Aza-Michael addition.

Step a) of the process of the present invention proceeds as a chain-growth polymerization. In one embodiment, step a) comprises radical copolymerization.

The type of copolymer formed by step a) of the present invention may be a statistical copolymer, a random copolymer, an alternating copolymer, a block copolymer or a combination thereof.

A copolymer obtained by step a) of the present invention is an amino group containing copolymer, such as, for example, a copolymer obtainable by copolymerization of acrylate and aminopropyl vinyl ether.

The reaction conditions of the polymerization reaction according to step a) of the present invention are not particularly limited. Accordingly, it is possible to carry out the reaction in the presence or absence of a solvent. A suitable solvent may be selected from the group of water, dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction is preferably carried out in the presence of a polymerization initiator. In a preferred embodiment of the process of the present invention, the polymerization initiator is selected from azobisisobutyronitrile (AIBN), 2,2-azobis (2-amidinopropane)dihydrochloride, 2,2'-azobis(2-methylbutyronitrile), 2,2'-azobis(N,N'-dimethyleneisobutyramidine)dihydrochloride, and 4,4'-azobis(4-cyano pentanoic acid). The amount of the polymerization initiator is not particularly limited. Suitably, the amount is in the range of from 0.001 to 5 mol % based on the total amount of the monomers.

The reaction product obtained in step a) may be isolated by precipitation and filtration. The product may be purified by washing with a suitable solvent.

Step b) of the process of the present invention is a step of coupling a compound having a polymerizable moiety and a functional group reactive with an amino group of repeating units derived from the second copolymerizable monomer in the amino group containing copolymer obtained in the first step wherein the optionally protected amino group is deprotected.

Preferably, the coupling reaction in step (b) is an addition reaction or a condensation reaction forming a bond selected from an amide bond, a urea bond or a thiourea bond.

By a functional group reactive with an amino group, herein is meant any group which can form a covalent bond with an amino group of the amino group containing copolymer. Preferably, a functional group reactive with an amino group is a carboxylic acid group or a derivative thereof such as an ester group or an anhydride thereof, an isocyanate group or an isothiocyanate group. More preferably, a functional group reactive with an amino group is a carboxylic acid group or a derivative thereof.

If the amino group of repeating units derived from the second copolymerizable monomer in the amino group containing copolymer obtained in the first step is protected, the amino group can be deprotected prior to step (b) or concomitant with step (b).

The conditions for deprotection of an optionally protected amino group have to be selected according to the protecting group used. Preferably, the protected amino group is deprotected by hydrogenolysis or treatment with acid or base.

If the deprotection of a protected amino group is carried out concomitantly with step (b), it will be understood by a person skilled in the art that the deprotection conditions and the conditions for step (b) have to be selected so that both reactions can proceed efficiently.

In a preferred embodiment of the process of the present invention, the compound having a polymerizable moiety and a functional group reactive with an amino group of repeating units derived from the second copolymerizable monomer is a compound of formula (3):

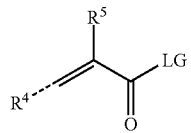

In formula (3), $R^4$ is a hydrogen atom or a straight chain or branched $C_{1-6}$ alkyl group which may be substituted by a —COOZ group and $R^5$ is a hydrogen atom or a straight-chain or branched $C_{1-5}$ alkyl group which may be substituted by a —COOZ group. Preferably, $R^4$ is a hydrogen atom and $R^5$ is a hydrogen atom or a methyl group. More preferably, $R^4$ is a hydrogen atom and $R^5$ is a methyl group. In formula (3), the dotted line indicates that $R^4$ may be in either the cis or trans orientation.

In formula (3), Z" which may be same or different, independently represents a hydrogen atom, a metal ion, a protecting group for a carboxylic acid group, or the Z" forms with a further —COOZ" group present in the molecule an intramolecular anhydride group.

In one embodiment, Z" is a protecting group for a carboxylic acid group. In another embodiment, Z" is a hydrogen atom. In a preferred embodiment, Z is a hydrogen atom and the polymerization reaction is conducted in an alkaline environment. In an alternative preferred embodiment, Z"s a hydrogen atom and the amino groups of the second copolymerizable monomer carry a protecting group.

In one embodiment, in formula (3), LG is a leaving group. Preferably, LG is a chlorine atom or a bromine atom, or forms with the adjacent carbonyl group a carboxylic acid anhydride moiety. Preferably, LG is a group which is suitable for reacting the compound of formula (3) in a Schotten-Baumann type reaction.

In another embodiment, LG may replace Z and form with $R^4$ or $R^5$ an intramolecular carboxylic acid anhydride group.

In yet another embodiment two molecules of formula (3) form an intermolecular carboxylic acid anhydride group by sharing a common LG, wherein LG is an oxygen atom.

Preferably, the compound having a polymerizable moiety and a functional group reactive with an amino group of repeating units derived from the second copolymerizable monomer forms a carboxylic acid anhydride group. More preferably, the compound forms an intermolecular carboxylic anhydride group with a second compound of formula (3). Most preferably, the compound forms (meth)acrylic anhydride.

The coupling according to step b) of the present invention serves to introduce one or more polymerizable moieties into the amino group containing copolymer, which moieties can be post-polymerized to provide additional covalent cross-linking, imparting additional strength to the dental material comprising the copolymer.

In one embodiment of the process of the present invention, the carboxylic acid groups of the copolymer obtained in step b) are not protected and the copolymer can be used as a polymer according to the present invention without further treatment. In an alternative embodiment, the carboxylic acid groups of the copolymer obtained in step b) are protected and the carboxylic acid groups have to be deprotected before the copolymer exhibits the features of a polymer according to the present invention.

The reaction conditions of the reaction according to step b) of the present invention are not particularly limited. Accordingly, it is possible to carry out the reaction in the presence or absence of a solvent. A suitable solvent may be selected from the group of dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction of step (a) s is preferably carried out in the presence of a polymerization initiator. In a preferred embodiment of the process of the present invention, the polymerization initiator is selected from azobisisobutyronitrile (AIBN), 2,2-azobis(2-amidinopropane)dihydrochloride, 2,2'-azobis(2-methylbutyronitrile), 2,2'-azobis(N,N'-dimethyleneisobutyramidine)dihydrochloride, and 4,4'-azobis(4-cyano pentanoic acid). The amount of the polymerization initiator is not particularly limited. Suitably, the amount is in the range of from 0.001 to 5 mol % based on the total amount of the monomers.

The reaction product obtained in step b) may be isolated by precipitation and filtration. The product may be purified by washing with a suitable solvent.

The process of the present invention optionally includes a step of deprotecting the protected carboxylic acid group after step (a) or step (b), for obtaining a polymerizable polymer. In a preferred embodiment, the process of the present invention includes a step of deprotecting the protected carboxylic acid group for obtaining a polymerizable polymer. In a further preferred embodiment, the process of the present invention includes a step of deprotecting the protected carboxylic acid group after step (b).

The conditions for deprotection of an optionally protected carboxyl group are selected according to the protecting group used. Preferably, the protected carboxyl group is deprotected by hydrogenolysis or treatment with acid or base.

A first embodiment of the process of the present invention is illustrated by the following scheme wherein a amino group protected vinyl amine is reacted with acrylic acid for obtaining a polymer backbone having a protected amino group. The copolymer is preferably a random copolymer. In a further step, the protected amino groups of the polymer backbone are liberated and coupled to a polymerizable group containing moiety, whereby a polymer of the invention is obtained having acidic groups reactive in a cement reaction wherein ionic bonds are formed, and having polymerizable groups reactive in a crosslinking reaction wherein covalent bonds are formed.

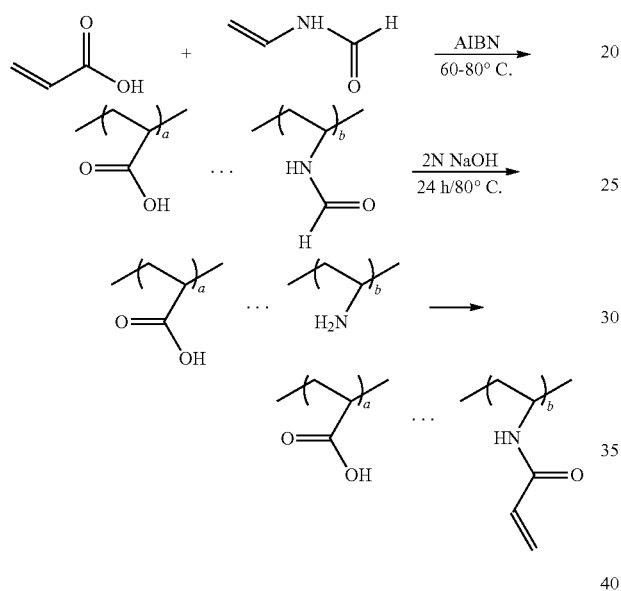

In the above scheme, any acrylamide group may be replaced by a methacrylamide group A second embodiment of the process of the present invention is illustrated by the following scheme wherein protected acrylic acid is reacted with an amino group containing polymerizable vinyl ether derivative for obtaining an amino group containing polymer backbone. In a further step, the amino groups of the polymer backbone are couples to a polymerizable group containing moiety. Finally, the carboxylic acid groups are liberated whereby a polymer of the invention is obtained having acidic groups reactive in a cement reaction wherein ionic bonds are formed, and having polymerizable groups reactive in a crosslinking reaction wherein covalent bonds are formed.

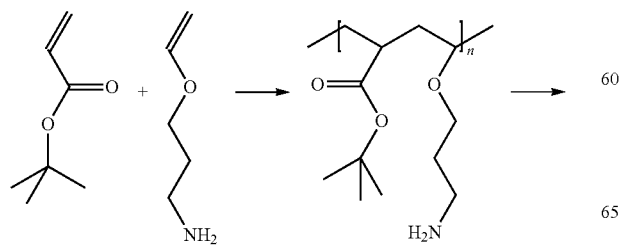

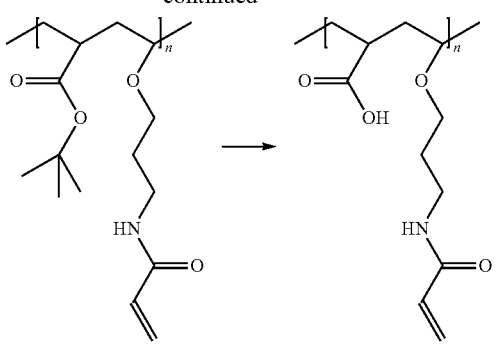

In the above scheme, any acrylamide group may be replaced by a methacrylamide group According to the present invention a novel polymer is provided. The polymer of the invention may be exemplified by the following preferred structures.

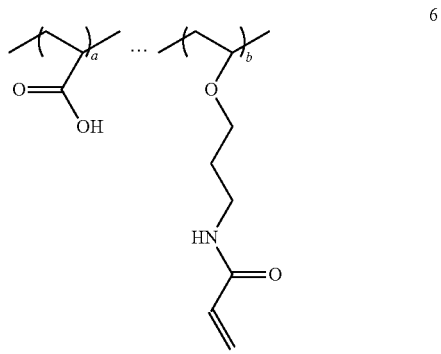

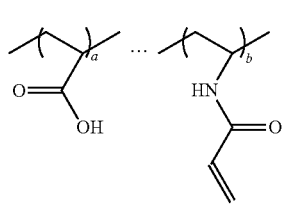

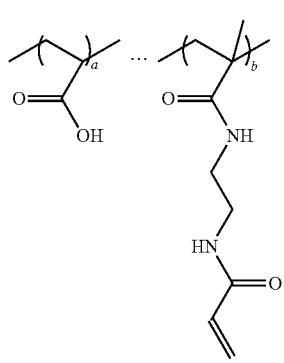

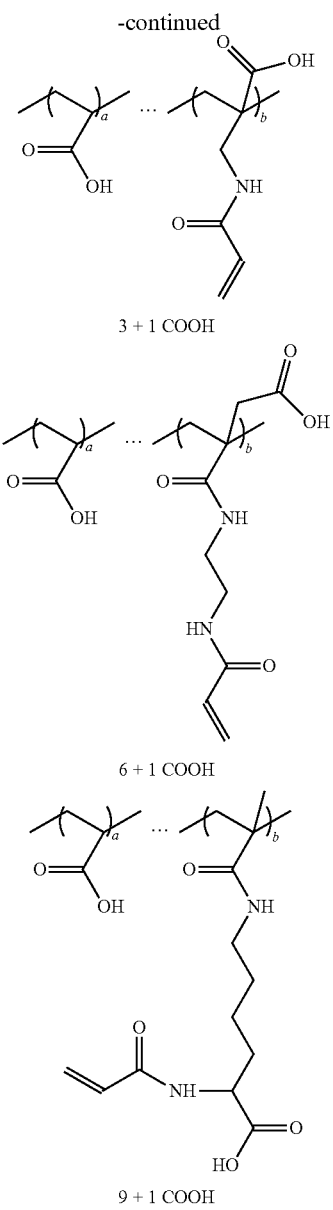

3 + 1 COOH

6 + 1 COOH

9 + 1 COOH

In the above structures, the numbers refer to the number of additional carbon atoms introduced by each of the side chain as compared to a corresponding polyacrylic acid. Since a polymer having (a+b) repeating units contains b times the number of additional carbon atoms in addition to the number of carbon atoms in a polyacrylic acid having (a+b) carboxylic acid groups, but b times less carboxylic acid groups, the water solubility may be reduced. On the other hand, the introduction of an additional ionic group such as a —COOH group is capable of compensating the decrease in water solubility, and is also indicated above. Preferably, the number of side chains b, the number of additional carbon atoms and the number of additional carboxylic acid groups are adjusted so as to provide a useful water solubility of the polymer of the present invention.

Accordingly, in a preferred embodiment, the side chains of the polymer which are linked to the polymer backbone via an amide bond, urea bond or thio urea bond contain one or more additional acidic groups, preferably carboxylic acid groups.

A polymerizable polymer according to the present invention, which is obtainable by the process as described above, is particularly useful for glass-ionomer cement (GIC) systems. A polymer according to the present invention preferably has an average molecular weight $M_w$ in the range of from 1,000, in particular 10,000 to 1,000,000 Da. More preferably, the average molecular weight $M_w$ is in the range of from 100,000 to 700,000 Da, or 50,000 to 250,000 Da.

The formation of such a cement, which is useful as a dental material, is based on a reaction between a reactive particulate filler, such as a powdered metal oxide or hydroxide, mineral silicate, or ion leachable glass or ceramic, and an ionic polymer, e.g. a polyalkenoic acid. Preferably, such a glass-ionomer cement is formed by reacting a polymer according to the present invention with a fluoroaluminosilicate glass (FAS glass).

Polymers to be used in such a system must be sufficient in number or percent by weight of carboxylic acid groups to bring about the setting or curing reaction in the presence of the modified particulate reactive and/or non-reactive filler.

A dental composition according to the present invention, comprises the polymer as described above and may additionally contain a particulate reactive and/or non-reactive filler, an initiator system, one or more additional comonomers.

Examples of reactive particulate filler materials include materials commonly known in the art of dental compositions such as calcium or strontium-containing and aluminum-containing materials. Preferably, particulate reactive fillers contain leachable fluoride ions. Specific examples of particulate reactive fillers are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive fillers further include metal oxides such as zinc oxide and magnesium oxide, and ion-leachable glasses, e.g., as described in U.S. Pat. No. 3,655,605, U.S. Pat. No. 3,814,717, U.S. Pat. No. 4,143,018, U.S. Pat. No. 4,209,434, U.S. Pat. No. 4,360,605 and U.S. Pat. No. 4,376,835.

Suitable non-reactive fillers may be selected from fillers currently used in dental restorative compositions.

The filler may have a unimodal or polymodal (e.g., bimodal) particle size distribution. The filler can be an inorganic material. It can also be a crosslinked organic material that is insoluble in the polymerizable resin, and is optionally filled with inorganic filler. The filler can be radiopaque, radiolucent or non-radiopaque. Examples of suitable non-reactive inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents includes gamma-methacryloxypropyltrimethoxysilane, gamma-mercaptopropyltriethoxysilane, gamma-aminopropyltrimethoxysilane, and the like.

The particulate filler usually has an average particle size of from 0.005 to 100 μm, preferably of from 0.01 to 40 μm as measured, for example, by electron microscopy or by using a conventional laser diffraction particle sizing method as embodied by a MALVERN Mastersizer S or MALVERN Mastersizer 2000 apparatus. The particulate filler may be a multimodal particulate reactive filler representing a mixture of two or more particulate fractions having different average particle sizes. The particulate reactive filler may also be a mixture of particles of different chemical composition. In particular, it is possible to use a mixture of a particulate reactive material and a particulate non-reactive material. The particulate reactive filler may be surface modified by a surface modifying agent.

As an initiator, any compound or system, capable of initiating the copolymerization reaction according to the present invention may be suitably used. The initiator may be based on a radical initiator and may be a photoinitiator or a redox initiator or a mixture thereof. A suitable photoinitiator may comprise camphor quinone/amine, or trimethylbenzoyl-diphenyl-phosphine oxide (TPO). A suitable redox initiator may be selected from benzoyl peroxide/amine, potassium peroxodisulfate ($K_2S_2O_8$)/ascorbinic acid, sodium peroxodisulfate, sodium pyrosulfite ($Na_2S_2O_5$)

A suitable comonomers contain at least one polymerizable functional group. Suitable polymerizable functional groups are ethylenically unsaturated groups (e.g. alkenyl groups and preferably vinyl groups). Preferred examples are substituted and unsubstituted acrylates, methacrylates, or alkenes.

A dental composition according to the present invention may also include a modifying agent such as tartaric acid, for adjusting the working time and a setting time of the glass ionomer cement reaction, respectively, when preparing the cement as described in U.S. Pat. No. 4,089,830, U.S. Pat. No. 4,209,434, U.S. Pat. No. 4,317,681 and U.S. Pat. No. 4,374,936. In general, an increase in working time results in an increase in setting time as well.

The "working time" is the time between the beginning of the setting reaction when the polymer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration.

In a setting reaction, due to the presence of polymerizable double bonds, a polymerization reaction takes place.

A dental composition according to the present invention may further contain solvents, pigments, nonvitreous fillers, free radical scavengers, polymerization inhibitors, bisacrylamides such as N,N'-diethyl-1,3-bisacrylamido-propan (BADEP), 1,3-bisacrylamido-propan (BAP), and 1,3-bisacrylamido-2-ethyl-propan (BAPEN), reactive and nonreactive diluents e.g., 2-hydroxyethyl methacrylate (HEMA), hydroxypropyl methacrylate, surfactants (such as to enhance solubility of an inhibitor e.g., polyoxyethylene), coupling agents to enhance reactivity of fillers e.g., 3-(trimethoxysilyl)propyl methacrylate, and rheology modifiers.

Suitable solvents or nonreactive diluents include alcohols such as ethanol and propanol. Suitable reactive diluents are alpha,beta unsaturated monomers for providing altered properties such as toughness, adhesion, and set time.

Suitable alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired. Preferably, the mixed but unset dental compositions of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset dental composition components.

An example of a suitable free radical scavenger is 4-methoxyphenol. An example of a suitable inhibitor is tert.-butyl hydroquinone (TBHQ), hydroxytoluene or butylated hydroxytoluene (BHT). The amount of inhibitor may be selected from 0.001 to 2% and preferably from 0.02 to 0.5% based on the total weight of the copolymer/comonomer/water mixture.

A polymer according to the present invention may be used for the preparation of a dental composition. The dental composition may be a dental material to be used in the oral cavity. Dental compositions according to the present invention are useful as restorative and filling materials, luting cements, adhesive cements, base or orthodontic cements, cavity liners and bases, pit and fissure sealants.

The invention will now be further illustrated by the following Examples.

EXAMPLES

Example 1

1. Copolymerisation of Tert.-Butylacrylat (tButA) and 3-Aminopropylvinylether (APVE) to Poly(tButA-co-APVE)

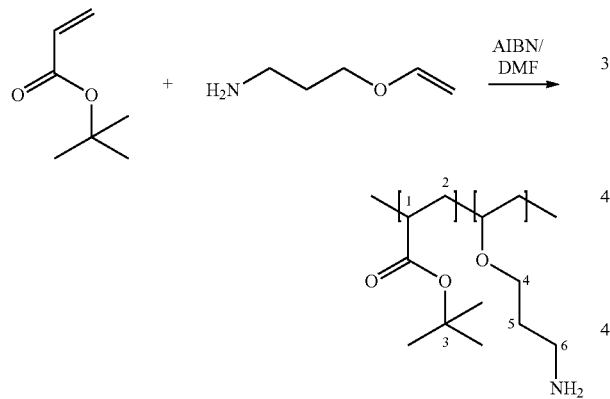

5.0 g (39 mmol) tButA, 0.99 g (9.8 mmol, 20 mol-%) APVE and 0.16 g (2 mol-%) AIBN were separately dissolved in DMF and the solutions were saturated with $N_2$. Then the solutions were combined and stirred for 24 h at 70° C. After the polymerization the cooled solution was diluted with DMF to 30 wt-% polymer solutions and precipitated in water/methanol (9:1). The separated solid was dried in vacuum.

The obtained copolymer had a molecular weight $M_n$=18 kDa, an $M_w$=51 kDa and a PD of 2.8.

IR-spectroscopy of the product showed no vinylether-vibrations while $^1$H-NMR showed broadened peaks for the aliphatic protons and no peaks for possible remaining double bond protons.

$^1$H-NMR (500 MHz, DMSO-$d_6$): δ (ppm)=3.5 (2H, 4), 2.7 (2H, 6), 2.2 (2H, 2), 1.8 (1H, 1), 1.6 (2H, 5), 1.44 (9H, 3).

2. Methacrylation of the Poly(tButA-co-APVE)

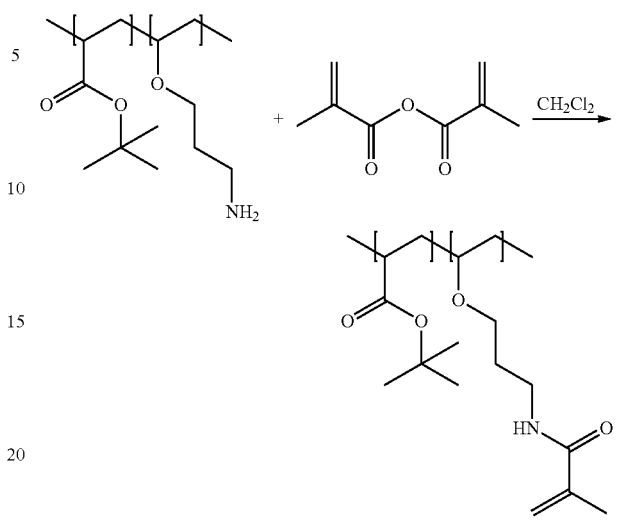

To a solution of 5 g (33.7 mmol) copolymer poly(tButA-co-APVE) dissolved in 31.5 g dichloromethane were added 1.3 g (8.42 mmol) methacrylic acid anhydride. After stirring the solution for 24 h at ambient temperature, the solvent was removed and the crude product was dissolved in 30 mL methanol. From this solution the polymer was precipitated in water, filtered off and dried in vacuum.

FT-IR: $v_{max}$ [cm$^{-1}$]=2976, 2932, 1785, 1722 (Ester), 1670 (Amid I), 1626 (C=C), 1526 (Amid II), 1479, 1448, 1392, 1366, 1143, 844.

3. Hydrolysis of Ester Moieties

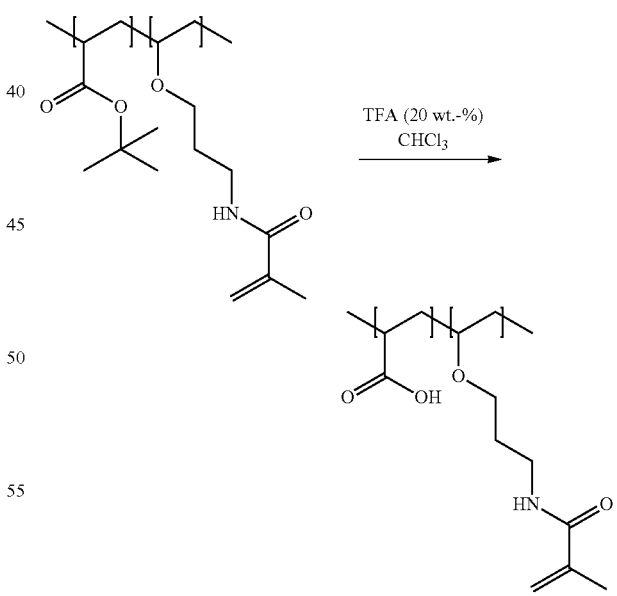

To a solution of 1.0 g (8.15 mmol) of the methacrylated poly(tButA-co-APVE) in 5 mL chloroform were added 20 wt-% trifluoro acetic acid. After stirring the solution for 5 h at 60° C. the crude precipitated polymer was separated from the solvent. The polymer was washed with chloroform, dissolved in methanol and re-precipitated in chloroform. Then the yellow polymer was dried in vacuum.

$^1$H-NMR (500 MHz, DMSO-d$_6$): δ (ppm)=12.2 (1H, —COOH), 7.8 (1H, —NH—), 5.6 (1H, —C=C—H), 5.3 (1H, C=C—H), 2.2 (2H, —CH2- backbone), 1.8 (3H, —CH$_3$), 1.8 (1H, —CH—, backbone), 1.5 (2H, O—CH$_2$CH$_2$), 1.4 (9H, C—(CH$_3$)$_3$, residual ester moieties).

Example 2

1. Copolymerization of Tert Butyl Acrylate (t-BA) and 3-Aminopropyl Vinylether (APVE) to Poly(AA-co-APVE)

In a three necked round bottom flask, equipped with a cooler, 2.34 mL (0.0206 mol) APVE and 8.97 mL (0.0618 mol) t-BA were mixed with 20 mL dioxane. 278 mg AIBN (2 mol-% regarding the total monomers) were dissolved, too. The reaction mixture was instantaneously flushed with Argon for about 20 min. Meanwhile a metal bath was preheated to 90° C. The polymerization was instantaneously started by placing the bath below the flask. After 1 h of stirring the reaction was complete. A sample of 5 mL was withdrawn and diluted with dioxane to 20 mL. The polymer was precipitated by adding this solution to an excess of 150 mL water. The polymer was dried at the vacuum pump. The molecular weight was determined by using SEC with DMF as eluent. $M_n$=11500 g/mol, $M_w$=38100 g/mol, PD=3.32

2. Modification of Poly(AA-co-APVE) with Methacrylic Anhydride

To the residue of the reaction mixture from synthetic step 1 cooled down to room temperature were added 26 mg tert.-butyl hydroquinone (TBHQ) to deactivate the residual initiator. Than 0.0309 mol methacrylic anhydride were added. After stirring the mixture for 2 h at room temperature, the solvent was removed at the rotary evaporator (30° C.) and afterwards the sample was dried at the vacuum pump. The NMR-spectra shows broadened peaks at 5.30 ppm and 5.64 ppm of double bonds indicating that the modification was successful.

3. Hydrolysis of Tert.-Butyl Ester Moieties 20 g of a polymer with 5 mol-% APVE incorporated were modified with methacrylic anhydride as described above. After removing the solvents at the rotary evaporator the crude product was dissolved in 50 mL of trifluoroacetic acid. The mixture was cooled in an ice bath which was slowly dissolving and stirred for 24 h. Over night the polymer precipitated. The suspension was decanted and the polymer was dissolved in 100 mL of dioxane. It was precipitated in a fivefold excess of acetone. The precipitate was dissolved again in dioxane and precipitated again. Afterwards the polymer was first dried at the rotary evaporator and afterwards at the vacuum pump. The NMR-spectra shows that the peak of the tert-butyl group at 1.38 ppm has nearly vanished. This corresponds to a degree of hydrolysis of 98 mol-%.

Example 3

Copolymerisation of Tert.-Butylacrylate and 3-Aminopropylvinylether—P(tBu-co-APVE)

A solution of 15 g (117 mmol) tert.-Butylacrylat in 38 g DMF was saturated under ice cooling with nitrogen. 3 g (29 mmol) 3-Amino-propylvinylether were added to this solution after 15 minutes. Further 5 minutes later were added 480 mg (2 mol-%) AIBN in nitrogen counter flow. Then the solution was stirred for 24 h at 70° C. After the polymerization the cooled solution was diluted with DMF to 33 wt-% polymer solutions and precipitated in the 20-fold quantity of water. The solid was filtered off, washed with water and dried in vacuum.

FT-IR: $v_{max}$ [cm$^{-1}$]=2977 (—CH$_2$—), 1723 (ester), 1481, 1449, 1392, 1366, 1255, 1144, 845.

$^1$H-NMR (500 MHz, CDCl$_3$): δ(ppm)=3.5 (2H, —O—CH$_2$—), 2.7 (2H, —CH$_2$—NH$_2$), 2.2 (2H, backbone), 1.8 (1H, backbone), 1.6 (2H, —O—CH$_2$—CH$_2$—), 1.44 (9H, -tbutyl).

GPC (DMF): $M_n$=26 kDa, $M_w$=70 kDa, $M_z$=124 kDa, PD=2.7.

The following table shows typical molecular masses for different polymerization samples using a ratio of eq(tBA):eq(APVE)=3:1:

| Batch # | c(AIBN) [mol-%] | $t_{term.}$ [min.] | $M_n$ | $M_w$ | $M_z$ | PD |
|---|---|---|---|---|---|---|
| 044-020 | 4 | 10 | 35.600 | 81.000 | 137.000 | 2.3 |
|  |  | 30 | 40.000 | 64.200 | 94.000 | 1.6 |
|  |  | 60 | 40.400 | 60.700 | 85.100 | 1.5 |
|  |  | 1440 | 36.000 | 65.200 | 97.300 | 1.8 |
| 044-022 | 1 | 10 | 14.900 | 37.400 | 72.900 | 1.9 |
|  |  | 30 | 14.800 | 39.200 | 71.700 | 1.8 |
|  |  | 60 | 150.800 | 160.200 | 166.400 | 1.0 |
| 044-023 | 0.1 | 30 | 69.700 | 106.900 | 146.400 | 1.5 |

Itaconic Amide Modified P(tBA-co-APVE-IA)

To a clear solution of 3.0 g p(tBA-co-APVE) in 10 mL dichloro methane were added portion wise under stirring 0.4 g (3.6 mmol) itaconic acid anhydride, whereby the solution discolorates red and then yellowish. Then the solution was stirred for 24 h at room temperature prior to evaporate dichloro methane.

FT-IR: $v_{max}$ [cm$^{-1}$]=2977 (—CH$_2$—), 1718 (ester), 1668 (amide I), 1559 (amide II), 1476, 1437, 1392, 1367, 1252, 1146, 1100, 945, 843.

Hydrolysis of Ester Moieties to P(AA-co-APVE-IA)

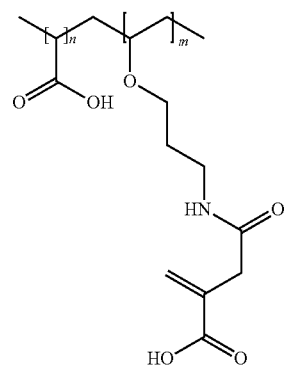

The modified polymer was added portion wise under stirring to 10 mL trifluoro acetic acid, and stirred some hours at room temperature prior to evaporate the trifluoro acetic acid in vacuum. The obtained high viscous polymer was dissolved in water and dialyzed for 4 days (MWCO=1000 g/mol). After frieze drying a reddish solid was received.

FT-IR: $v_{max}$ [cm$^{-1}$]=3392, 2932 (—CH$_2$—), 1699 (acid), 1625 (—C=C), 1546 (amide II), 1447, 1407, 1230, 1164, 1094, 934, 798, 610

$^1$H-NMR (300 MHz, D$_2$O): δ (ppm)=8.0 (1H, —NH—), 6.4 (1H, —C=C—H), 5.6 (1H, —C=C—H), 3.5 (2H, —O—CH$_2$—), 3.4 (2H, —NH—CH$_2$—), 3.3 (2H, —NH—CO—CH$_2$), 2.4 (1H, backbone), 2.0-1.5 (2H, backbone), 1.6 (2H, —O—CH$_2$—CH$_2$—).

Example 4

Methacrylamide Modified P(tBA-co-APVE-MA)

To a clear solution of 3.0 g p(tBA-co-APVE) of example 4 dissolved in 10 mL dichloro methane were added drop wise 0.6 g (4.1 mmol) methacrylic acid anhydride. Then the solution was stirred for 24 h at room temperature prior to evaporate dichloro methane. The obtained raw product was applied for further reactions without purification.

FT-IR: □$_{max}$ [cm$^{-1}$]=3351, 2977 (—CH$_2$—), 1721 (ester), 1668 (amide I), 1622 (—C=C), 1531 (amide II), 1452, 1392, 1366, 1255, 1146, 1089, 940, 845.

Hydrolysis of Ester Moieties to P(AA-co-APVE-MA)

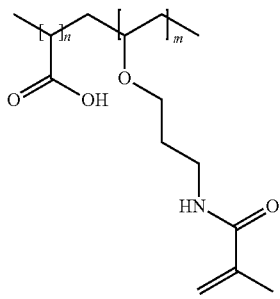

The modified polymer was added portion wise under stirring to 10 mL trifluoro acetic acid, and stirred some hours at room temperature prior to evaporate the trifluoro acetic acid in vacuum. The obtained high viscous polymer was dissolved in water and dialyzed for 4 days (MWCO=1000 g/mol). After frieze drying a colorless solid was received.

FT-IR: ν$_{max}$ [cm$^{-1}$]=3180, 2934 (—CH$_2$—), 2613, 1701 (acid), 1650 (amide I), 1597, 1537 (amide II), 1449, 1408, 1211, 1162, 1110, 919, 797, 611

$^1$H-NMR (300 MHz, D$_2$O): δ (ppm)=8.0 (1H, —NH—), 5.7 (1H, —C=C—H), 5.4 (1H, —C=C—H), 3.5 (2H, —O—CH$_2$—), 3.5 (2H, —NH—CH$_2$—), 2.2 (1H, backbone), 1.8-1.6 (2H, backbone), 1.6 (2H, —O—CH$_2$—CH$_2$—).

Example 5

Acrylamide Modified P(tBA-co-APVE-AA)

To a solution of 5.0 g p(tBA-co-APVE) of example 4 dissolved in 30 mL THF were added under ice cooling drop wise 0.76 g (6.7 mmol) acryloyl chloride, whereby immediately a white solid precipitates. The reaction mixture was stirred for further 24 h at room temperature. The solid was filtered off and the solvent was evaporated. The crude raw material was used for hydrolysis without further purification.

FT-IR: ν$_{max}$ [cm$^{-1}$]=3289, 2976 (—CH$_2$—), 1722 (ester), 1659 (amide I), 1628 (—C=C), 1544 (amide II), 1480, 1448, 1366, 1254, 1143, 844.

Hydrolysis of Ester Moieties to P(AA-co-APVE-AA)

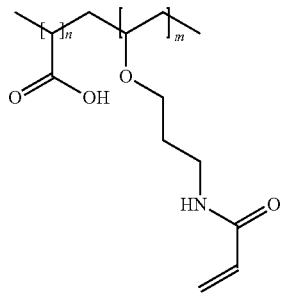

3 g of the modified polymer was added portion wise under stirring to 10 mL trifluoro acetic acid, and stirred some hours at room temperature prior to evaporate the trifluoro acetic acid in vacuum. The obtained high viscous polymer was dissolved in water and adjusted to pH 2 by addition of aqueous NaOH. Then the solution was dialyzed for 4 days (MWCO=1000 g/mol). After frieze drying a colorless solid was received.

FT-IR: ν$_{max}$ [cm$^{-1}$]=3361, 2930 (—CH$_2$—), 1707 (acid), 1654 (amide I), 1620 (—C=C), 1544 (amide II), 1447, 1407, 1242, 1179, 1097, 980, 801.

$^1$H-NMR (300 MHz, D$_2$O): δ (ppm)=6.3 (1H, —C=C—H), 6.2 (1H, —C=C—H), 5.8 (1H, —CH=C<), 3.6 (2H, —O—CH$_2$—), 3.3 (2H, —NH—CH$_2$—), 2.2 (1H, backbone), 1.9-1.4 (2H, backbone), 1.6 (2H, —O—CH$_2$—CH$_2$—).

Example 6

Copolymerisation of Acrylic Acid and N-Vinyl Formamide[1] to P(AA-NVFA)

[1] N. A. Nesterova et alter, *Russian Journal of Applied Chemistry* 2008, Vol. 82, No. 4, pp. 618-621

3 g (41.6 mmol) acrylic acid and 590 mg (8.9 mmol) N-Vinylformamide were dissolved in 10.88 g distilled isopropanol and aerated with nitrogen for 30 minutes. Then 164 mg (2 mol-%) AIBN were added in the nitrogen counter flow and aerated with nitrogen for further 15 minutes. Then the solution was stirred for 24 h at 70° C., whereby a colorless solid precipitated. The solid was filtered off and washed repeatedly with acetone and dried under reduced vacuum. One obtained a colorless, fine dispersed solid.

FT-IR: ν$_{max}$ [cm$^{-1}$]=3272 (—NH$_2$), 3054 (—CH$_2$—), 2922, 1708 (acid), 1643 (amide I), 1532 (amide II), 1444, 1385 (—CH$_2$—), 1244, 1178.

$^1$H-NMR (300 MHz, DMSO-d$_6$): δ (ppm)=12.2 (1H, —COOH), 7.9 (1H, —NH—COH), 4.3 (1H, —CH—NH), 2.2 (1H, —CH—COOH), 1.7 (2H, —CH$_2$—CH—NH—), 1.5 (2H, CH$_2$—CHCOOH).

GPC(H$_2$O): M$_n$=10 kDa, M$_w$=49 kDa, M$_z$=126 kDa, PD=5.0.

Conversion of P(AA-co-NVFA) into P(AA-co-VAm)

(based on the hydrolysis of pure p(VFA) to provide p(VAm), in K. Yamamoto et alter, *Journal of Applied Polymer Science* 2002, Vol. 89, pp. 1277-1283.

200 mg of the copolymer p(AA-co-NVFA) were dissolved in 10 mL 2 N NaOH and stirred for 2 h at 100° C. Then the solution was neutralized by HCl and dialyzed for 3 days (MWCO=1000 g/mol). After freeze drying a fleece-like colorless solid was obtained.

FT-IR: $\square_{max}$ [cm$^{-1}$]=3274 (—NH$_2$), 2919 (—CH2-), 1666 (—COONa), 1559 (—NH$_2$), 1448, 1408 (—CH$_2$—), 1188 (—C—O—).

$^1$H-NMR (300 MHz, D$_2$O): δ (ppm)=2.5 (1H, —CH—NH$_2$), 2.0 (1H, —CH—COOH), 1.4 (2H, —CH$_2$—CH—NH$_2$), 1.3 (2H, —CH$_2$—CH—COOH).

Acrylamide Modified P(AA-co-VAm-MA)

0.5 g of the hydrolyzed copolymer P(AA-co-VAm) were added to a round bottom flask and an excess of 1.0 g methacrylic anhydride were added. The mixture was heated to 60° C. for 4 hours. Then the product was diluted in water and the polymer was precipitated in methanol twice. The final polymer was analyzed for functionalization with double bonds by $^1$H-NMR(C=C bonds at 5.51 ppm and 5.31 ppm). The polymer is soluble in water after stirring for 24 hours. The degree of functionalization reaches 4.0 mol-%.

Example 7

Copolymerisation of Acrylic Acid and N-(2-Amino Ethyl) Methacryl Amide Hydrochloride 0.2 g (3 mmol) acrylic acid and 0.5 g (3 mmol) N-(2-amino ethyl)methacryl amide hydrochloride were dissolved in 1.4 g DMF and aerated with nitrogen for 15 minutes. Then 20 mg (2 mol-%) VA-044 were added in the nitrogen counter flow and aerated with nitrogen for further 5 minutes. Then the solution was stirred for 2 h at 70° C., whereby a colorless solid precipitates. The solid was filtered off and washed repeatedly with acetone and dried under reduced vacuum. One obtained a colorless, fine dispersed solid.

FT-IR: $\square_{max}$ [cm$^{-1}$]=3350 (—NH$_2$), 2926, 1705 (acid), 1629 (amide I), 1527 (amide II), 1482, 1456, 1393, 1365, 1232, 1166, 837.

$^1$H-NMR (300 MHz, DMSO-d$_6$): δ (ppm)=12.3 (1H, —OH), 8.3 (1H, —NH—), 7.9 (2H, —NH$_2$), 4.2 (1H, CH3-CH<), 2.9 (2H, —NH—CH$_2$—), 2.6 (2H, —NH—CH$_2$—CH$_2$—), 1.5 (1H, backbone), 1.2 (3H, —CH$_3$), 1.0 (2H, backbone).

The invention claimed is:

1. A process for producing a water-soluble, hydrolysis-stable, polymerizable polymer, comprising a) a step of copolymerizing a mixture comprising (i) a first copolymerizable monomer comprising at least one protected carboxylic acid group or unprotected carboxylic acid group and a first polymerizable organic moiety, and (ii) a second copolymerizable monomer comprising one or more protected or unprotected primary and/or secondary amino groups and a second polymerizable organic moiety, for obtaining an amino group containing copolymer; b) a step of coupling to the amino group containing copolymer a compound having a polymerizable moiety and a functional group reactive with an amino group of repeating units derived from the second copolymerizable monomer in the amino group containing copolymer obtained in the first step, wherein the protected amino group is deprotected, so that polymerizable pendant groups are linked to the backbone by hydrolysis-stable linking groups, (c) further including a step of deprotecting any of the protected carboxylic acid group after step (a) or step (b), for obtaining a polymerizable polymer.

2. The process according to claim 1, wherein the molar ratio of first copolymerizable monomer and second copolymerizable monomer in the mixture copolymerized in step (a) (mol first copolymerizable monomer/mol second copolymerizable monomer) is in the range of from 100:5 to 5:100.

3. The process according to claim 1, wherein the coupling reaction in step (b) is an addition reaction or a condensation reaction forming a bond selected from an amide bond, a urea bond or a thiourea bond.

4. The process according claim 1, wherein the second polymerizable organic moiety of the second copolymerizable monomer is selected from the group of (meth)acrylamide moieties which may be substituted and substituted (meth)acrylic acid which may be protected.

5. The process according to claim 1 wherein the first copolymerizable monomer is a protected (meth)acrylic acid monomer.

6. The process according to claim 1 wherein the protecting group for a carboxylic acid group of the first copolymerizable monomer and second copolymerizable monomer is selected from a trialkylsilyl group, an alkyl group, and an arylalkyl group, or wherein the protecting group for an amino group of the first copolymerizable monomer and second copolymerizable monomer is selected from an acyl group, an arylalkyl group, an alkoxy carbonyl group, and an aryloxycarbonyl group.

7. The process according to claim 1, wherein the first copolymerizable monomer is represented by the general formula (1):

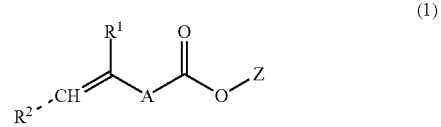

wherein R$^1$ is a hydrogen atom, a —COOZ group or a straight chain or branched C$_{1-6}$ alkyl group which may be substituted by a —COOZ group; R$^2$ is a hydrogen atom, a —COOZ group or a straight-chain or branched C$_{1-6}$ alkyl group which may be substituted by a —COOZ group; A is a single bond or a straight-chain or branched C$_{1-6}$ alkylene group which group may contain 1 to 3 heteroatoms in between two carbon atoms of the alkylene carbon chain, which heteroatoms are selected from an oxygen atom, nitrogen atom, and sulfur atom, and/or which alkylene group may contain in between two carbon atoms of the alkylene carbon chain 1 to 3 groups selected from an amide bond or a urethane bond; Z which may be the same or different, independently represents a hydrogen atom, a metal ion, a protecting group for a carboxylic acid group, or the Z forms with a further —COOZ group present in the molecule an intramolecular anhydride group.

8. The process according to claim 1, wherein the second copolymerizable monomer is represented by the general formula (2):

wherein R$^3$ is a hydrogen atom or a straight chain or branched C$_{1-6}$ alkyl group which may be substituted by a —COOZ' group; X is a protected amino group or a hydrocarbon group having 1 to 20 carbon atoms, which is substituted with an amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups; Y is a hydrogen atom, a —COOZ' group, or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups; Z' which may be the same or different, independently represents a hydrogen atom, a metal ion, a protecting group for a carboxylic acid group, or the Z' forms with a further —COOZ' group present in the molecule an intramolecular anhydride group.

9. The process according to claim 1 wherein the compound having a polymerizable moiety and a functional group reactive with an amino group of repeating units derived from the second copolymerizable monomer is a compound of formula (3):

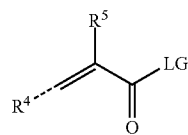

(3)

wherein $R^4$ is a hydrogen atom or a straight chain or branched $C_{1-6}$ alkyl group which may be substituted by a —COOZ" group; $R^5$ is a hydrogen atom or a straight-chain or branched $C_{1-6}$ alkyl group which may be substituted by a —COOZ" group; Z" which may be same or different, independently represents a hydrogen atom, a metal ion, a protecting group for a carboxylic acid group, or the Z" forms with a further —COOZ" group present in the molecule an intramolecular anhydride group; and LG is a leaving group, or wherein LG may replace Z" and form with $R^4$ or $R^5$ an intramolecular carboxylic acid anhydride group, or wherein two molecules of formula (3) form an intermolecular carboxylic acid anhydride group by condensation of LG and/or —COOZ", wherein LG is an oxygen atom.

10. The process according to claim 1, wherein the protecting group for a carboxylic acid is selected from a tert-butyl group and a benzyl group.

11. The process according to claim 1, wherein the second copolymerizable monomer is selected from allyl amine, aminopropyl vinyl ether, aminoethyl vinyl ether, N-vinyl formamide, and 2-aminomethyl acrylic acid.

12. A process for producing a water-soluble, hydrolysis-stable, polymerizable polymer, comprising a) a step of copolymerizing a mixture comprising (i) a first copolymerizable monomer comprising at least one protected carboxylic acid group or unprotected carboxylic acid group and a first polymerizable organic moiety, and is represented by the general formula (1):

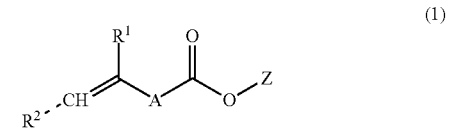

(1)

wherein $R^1$ is a hydrogen atom, a —COOZ group or a straight chain or branched $C_{1-6}$ alkyl group which may be substituted by a —COOZ group; $R^2$ is a hydrogen atom, a —COOZ group or a straight-chain or branched $C_{1-6}$ alkyl group which may be substituted by a —COOZ group; A is a single bond or a straight-chain or branched $C_{1-6}$ alkylene group which group may contain 1 to 3 heteroatoms in between two carbon atoms of the alkylene carbon chain, which heteroatoms are selected from an oxygen atom, nitrogen atom, and sulfur atom, and/or which alkylene group may contain in between two carbon atoms of the alkylene carbon chain 1 to 3 groups selected from an amide bond or a urethane bond; Z which may be the same or different, independently represents a hydrogen atom, a metal ion, a protecting group for a carboxylic acid group, or the Z forms with a further —COOZ group present in the molecule an intramolecular anhydride group; and, (ii) a second copolymerizable monomer comprising one or more protected or unprotected primary and/or secondary amino groups and a second polymerizable organic moiety, for obtaining an amino group containing copolymer, and is represented by the general formula (2):

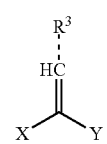

(2)

wherein $R^3$ is a hydrogen atom or a straight chain or branched $C_{1-6}$ alkyl group which may be substituted by a —COOZ' group; X is a protected amino group or a hydrocarbon group having 1 to 20 carbon atoms, which is substituted with an amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups; Y is a hydrogen atom, a —COOZ' group, or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups; Z' which may be the same or different, independently represents a hydrogen atom, a metal ion, a protecting group for a carboxylic acid group, or the Z' forms with a further —COOZ' group present in the molecule an intramolecular anhydride group;

b) a step of coupling to the amino group containing copolymer a compound having a polymerizable moiety and a functional group reactive with an amino group of repeating units derived from the second copolymerizable monomer in the amino group containing copolymer obtained in the first step, wherein the protected amino group is deprotected, so that polymerizable pendant groups are linked to the backbone by hydrolysis-stable linking groups; and (c) further including a step of deprotecting any of the protected carboxylic acid group after step (a) or step (b), for obtaining a polymerizable polymer;

wherein the compound having a polymerizable moiety and a functional group reactive with an amino group of repeating units derived from the second copolymerizable monomer is a compound of formula (3):

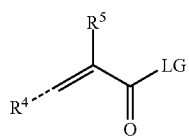

(3)

wherein $R^4$ is a hydrogen atom or a straight chain or branched $C_{1-6}$ alkyl group which may be substituted by a —COOZ" group; $R^5$ is a hydrogen atom or a straight-chain or branched $C_{1-6}$ alkyl group which may be substituted by a —COOZ" group; Z" which may be same or different, independently represents a hydrogen atom, a metal ion, a protecting group for a carboxylic acid group, or the Z" forms with a further —COOZ" group present in the molecule an intramolecular anhydride group; and LG is a leaving group, or wherein LG may replace Z" and form with $R^4$ or $R^5$ an intramolecular carboxylic acid anhydride group, or wherein two molecules of formula (3) form an intermolecular carboxylic acid anhydride group by condensation of LG and/or —COOZ", wherein LG is an oxygen atom.

13. The process according to claim 1, wherein the first copolymerizable monomer is selected from tert-butyl acrylate and benzyl acrylate.

\* \* \* \* \*